`US010888846B2`

United States Patent
Koehler et al.

(10) Patent No.: US 10,888,846 B2
(45) Date of Patent: Jan. 12, 2021

(54) MANGANESE-DOPED NICKEL-METHANATION CATALYSTS

(71) Applicant: CLARIANT PRODUKTE (DEUTSCHLAND) GMBH, Frankfurt am Main (DE)

(72) Inventors: Klaus Koehler, Ismaning (DE); Oliver Thomys, Neufahrn bei Freising (DE); Kai-Olaf Hinrichsen, Eichenried (DE); Franz Koschany, Mering (DE); Thomas Burger, Langenbach (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 0 days.

(21) Appl. No.: 16/479,283

(22) PCT Filed: Jan. 26, 2018

(86) PCT No.: PCT/EP2018/051996
§ 371 (c)(1),
(2) Date: Jul. 19, 2019

(87) PCT Pub. No.: WO2018/141649
PCT Pub. Date: Aug. 9, 2018

(65) Prior Publication Data
US 2019/0381486 A1 Dec. 19, 2019

(30) Foreign Application Priority Data

Jan. 31, 2017 (DE) .......................... 10 2017 000 874

(51) Int. Cl.
| | | |
|---|---|---|
| *B01J 23/889* | (2006.01) | |
| *B01J 21/04* | (2006.01) | |
| *B01J 35/00* | (2006.01) | |
| *B01J 35/10* | (2006.01) | |
| *B01J 37/02* | (2006.01) | |
| *B01J 37/03* | (2006.01) | |
| *B01J 37/06* | (2006.01) | |
| *B01J 37/08* | (2006.01) | |
| *C07C 1/04* | (2006.01) | |
| *C07C 1/12* | (2006.01) | |

(52) U.S. Cl.
CPC ........... *B01J 23/8892* (2013.01); *B01J 21/04* (2013.01); *B01J 35/006* (2013.01); *B01J 35/0053* (2013.01); *B01J 35/1019* (2013.01); *B01J 37/0236* (2013.01); *B01J 37/031* (2013.01); *B01J 37/06* (2013.01); *B01J 37/088* (2013.01); *C07C 1/0435* (2013.01); *C07C 1/0445* (2013.01); *C07C 1/12* (2013.01); *C07C 2521/04* (2013.01); *C07C 2523/755* (2013.01); *C07C 2523/889* (2013.01)

(58) Field of Classification Search
CPC ...... B01J 23/8892; B01J 21/04; B01J 35/006; B01J 23/755; B01J 23/74; C07C 2521/04; C07C 2523/755; C07C 1/12
See application file for complete search history.

(56) References Cited

U.S. PATENT DOCUMENTS

| | | | | |
|---|---|---|---|---|
| 4,233,179 A | * | 11/1980 | Russ | ..................... B01J 23/8892 252/373 |
| 4,354,960 A | | 10/1982 | Hammer | |
| 2010/0168257 A1 | | 7/2010 | Duisberg | |

FOREIGN PATENT DOCUMENTS

| | | |
|---|---|---|
| CN | 101745401 | 6/2010 |
| CN | 102091629 | 6/2011 |
| CN | 102463119 | 5/2012 |
| CN | 102463120 | 5/2012 |
| CN | 102513124 | 6/2012 |
| CN | 102527405 | 7/2012 |
| CN | 102553610 | 7/2012 |
| CN | 102600860 | 7/2012 |
| CN | 103464163 | 12/2013 |
| CN | 103480375 | 1/2014 |
| CN | 103706366 | 4/2014 |
| CN | 103752315 | 4/2014 |
| CN | 104028270 | 9/2014 |
| CN | 104043454 | 9/2014 |
| CN | 104888783 | 9/2015 |
| CN | 106268858 A | 1/2017 |
| JP | H3263492 | 11/1991 |
| JP | 2005238131 | 9/2005 |

OTHER PUBLICATIONS

Sunhwan Hwang, Methanation of Carbon dioxide over mesoporous Ni—Fe—Al2O3 catalysts prepared by a coprecipitatin method: Effect of precipitation agent; Journal of Industrial and Engineering Chemistry 19 (2013) 2016-2021.
Anmin Zhao, Ni/Al2O3 catalysts for sygas methanantion: Effect of MN promoter, Jourunal of Natural Gas Chemistry (2012) 21, 170-177.
Xiaoqing Gao, "Effect of Manganese Promoter on the Catalytic Performance of . . ." Journal of Molecular Catalysis (China) 25(1) 2011.
Sunhwan Hwang, "Methanation of carbon dioxide over mesoporous . . ." Catal. Lett 142 (2012) 860-868.
Sunhwan Hwang, "Methanation of carbon dioxide over mesoporous Ni—Fe—Al2O3 catalysts prepared by . . ." Journal of Industrial and Engineering Chemistry 19 (2013) 2016-2021.

(Continued)

*Primary Examiner* — Jafar F Parsa

(57) ABSTRACT

A methanation catalyst for the methanation of carbon monoxide and/or carbon dioxide is disclosed that provides high selectivity and stability, and additionally shows improved activity compared with prior catalysts. The methanation catalyst for the methanation of carbon monoxide and/or carbon dioxide comprises aluminum oxide, a Ni active mass, and Mn, wherein the Ni/Mn molar ratio in the catalyst is 3.0 to 10.0.

12 Claims, 5 Drawing Sheets

(56) References Cited

OTHER PUBLICATIONS

Figure 1:
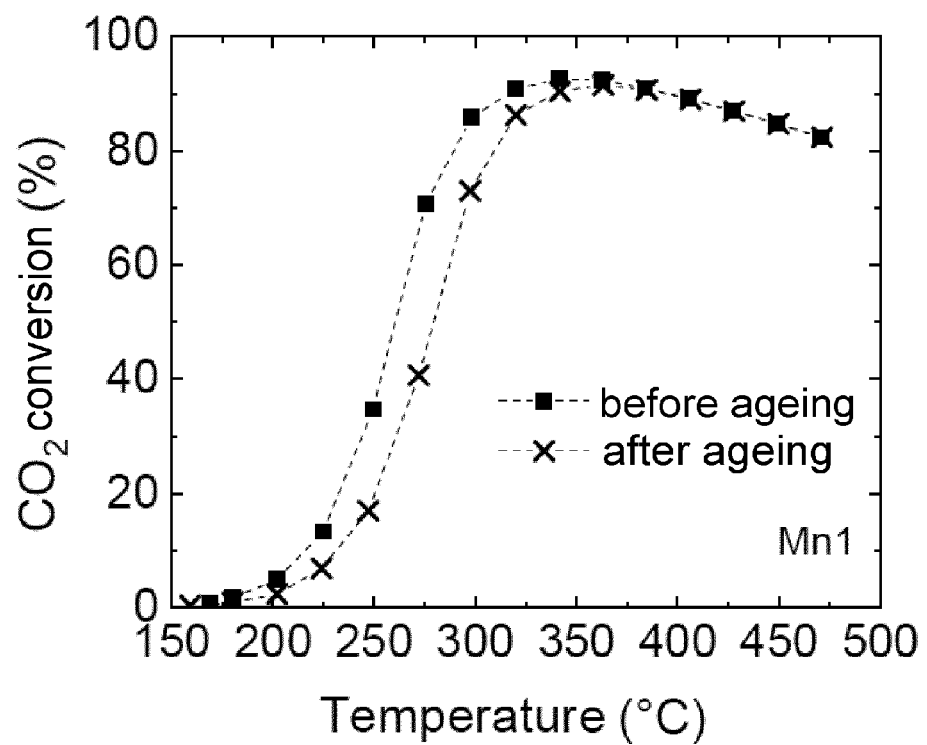
Figure 2:
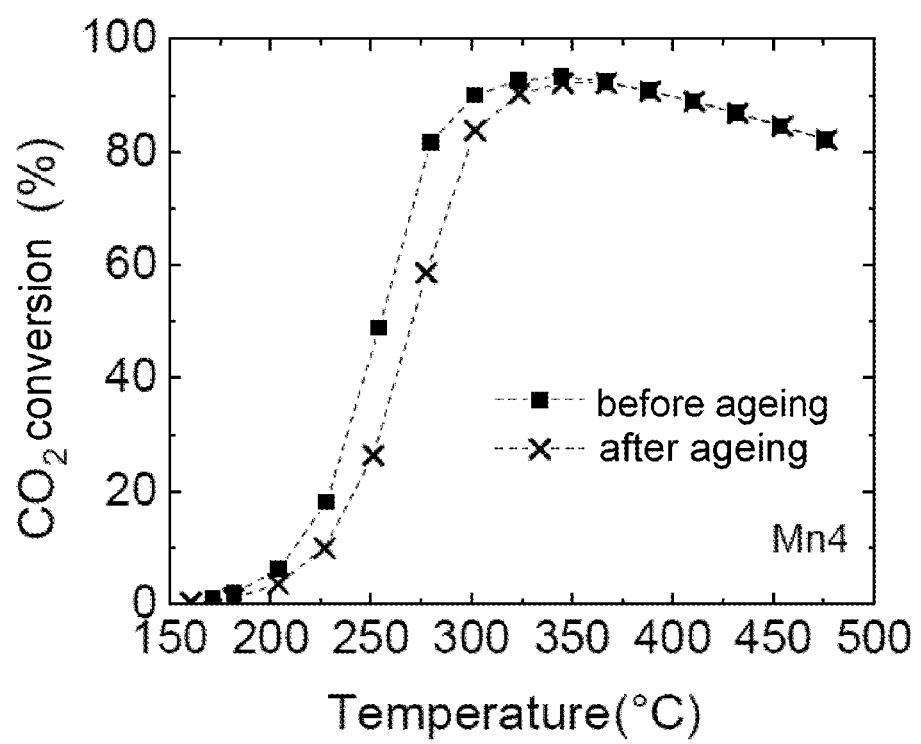
Figure 3:
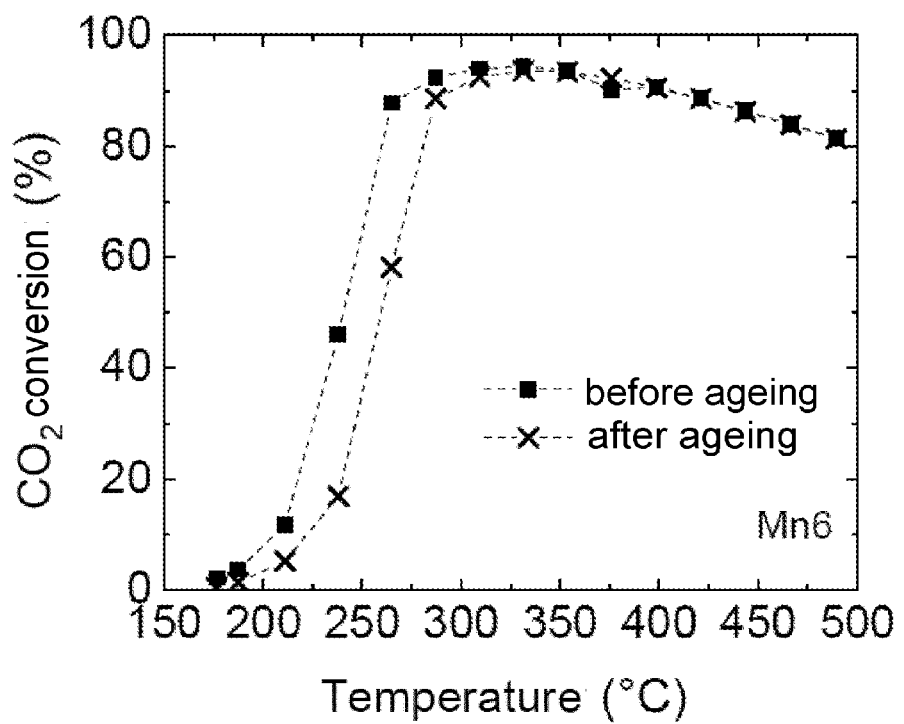
Figure 4:
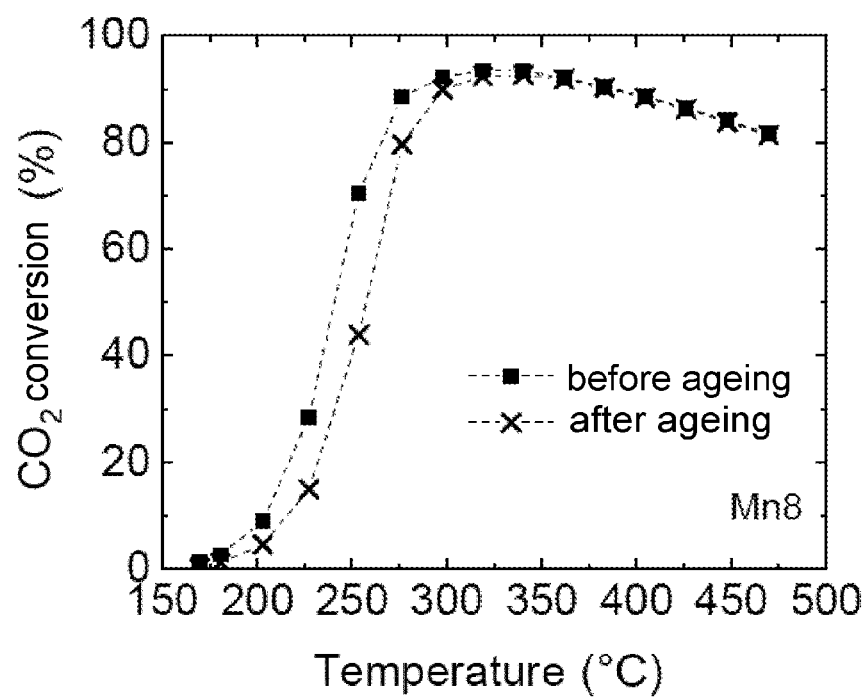

Wan Azelle, "Nickel Oxide Based SupPorted Catalysts . . ." Catal. Lett 128 (2009) 127-136.
Zhao Kechao, "CO2 methanation and co-methanation of CO and Co2over Mn-promoted . . ." Front. Chem. Sci Eng. 10(2), (2016) 273-280.

* cited by examiner

MANGANESE-DOPED NICKEL-METHANATION CATALYSTS

The supply of energy through the so-called renewable energies of photovoltaics and wind energy suffers from the problem of fluctuations in power production due to weather and time of day. To ensure security of supply, a way must be found that absorbs fluctuations in power production due to weather and time of day. One potential method of storing energy chemically is the power-to-gas process, in which surplus power is used to cleave water electrolytically into hydrogen and oxygen. Hydrogen, in which the energy obtained by electrolysis of water is stored, can itself be stored or transported to the end user only at high expense. In the power-to-gas process, the hydrogen therefore undergoes a methanation reaction to methane and water in a further reaction step with carbon dioxide, which in the atmosphere acts as a climate-damaging greenhouse gas. Methane can be easily stored in existing infrastructure, which has storage capacity for periods of months, can be transported long distances with almost zero losses, and can be converted back to power as and when required. The methanation reaction, which is associated with high energy release and is usually catalyzed, is the cornerstone of the process. The high exothermicity of the reaction (−165 kJ/mol) gives rise to two direct problems. Firstly, at high temperatures, the thermodynamic equilibrium places limits on the maximum methane yield that can be achieved. For methane to be fed into the natural gas grid in Germany, a purity of 95% is necessary. This necessitates catalysts with high activity that allow higher methane yields to be achieved at the reaction pressures and low temperatures employed in industry.

When reactors are operated adiabatically, the high exothermicity of the methanation reaction can sometimes cause hotspots to develop in the reactor. This can result in high local temperatures being reached that can damage the catalyst. To minimize the cost of catalyst replacement/shutdown times and material costs, there is accordingly high interest in developing catalyst systems that are as stable as possible. The need also arises for catalysts for the $CO_2$ methanation reaction that are as active and selective as possible.

The methanation reaction uses mainly nickel-based catalysts, but there are also approaches using other active metals, for example ruthenium or rhodium. As the support, in addition to aluminum oxide, oxides of silicon, titanium, and zirconium are also used. Descriptions of such systems are given, for example, in published patent applications CN 104043454 A, CN 103480375 A, CN 102091629 A, CN 104888783 A, and WO 2008110331 A1.

There are additionally catalysts that not only contain an active metal, but include promoters. As disclosed in the literature, promotion with iron or manganese can have a beneficial effect on catalyst performance.

Doping with manganese is described, for example, in CN 103464163 A, CN 103752315 A, CN 102600860 A, CN 102553610 A, CN 102527405 A, CN 102513124 A, CN 102463120 A, CN 102463119 A, CN 103706366 A, CN 104028270 A, and CN 101745401 A and by Zhao et al., Journal of Natural Gas Chemistry (2012), 21(2), 170-177 and Gao et al. Journal of molecular catalysis (China), vol. 25, No. 1, February 2011.

CN 103752315 A relates to a catalyst present on a metallic support phase and also the method of preparation and use of the catalyst in the production of methane and synthetic methane gas production through the catalytic conversion of carbon monoxide and/or carbon dioxide. The catalyst present on the metallic support phase comprises as active component a metal oxide present on the metallic support phase and an auxiliary metal oxide; the formula of the catalyst present on the metallic support phase is xM1O-yM2O/ZT, where M1O is the metal oxide as active component, ZT the metallic support phase, x the percentage by weight of the metal oxide as active component in the catalyst, and y is the percentage by weight of the auxiliary metal oxide.

CN 102600860 A relates to a catalyst that is suitable for the complete methanation of synthesis gas at moderate or lower temperatures. The catalyst comprises the following components in percent by weight: 12 to 26% nickel, 1 to 4% manganese, 0.1 to 2% of one or more of lanthanum, calcium and/or magnesium, the balance being a composite support containing aluminum oxide and cerium oxide, wherein the sum of the percentages by weight of the components is 100% and the cerium oxide content of the composite support is 6 to 12%. The catalyst is prepared by the steps: (1) formation of the composite support; (2) preparation of the impregnation solution; (3) treatment by a modified pressure impregnation method; and (4) heating the impregnated catalyst to 500 to 600° C. and calcining for 6 to 8 hours to obtain the desired product.

CN 102527405 A discloses a catalyst used for the complete methanation of synthesis gas at high temperature, wherein the catalyst comprises the following constituents in percent by weight: 10 to 30% by weight nickel, 11 to 20% by weight lanthanum, 1 to 5% by weight cerium, 0.1 to 2% by weight of one or more of manganese, lithium, and vanadium, with the balance comprising aluminum oxide, the sum of the percentages by weight of these constituents being 100%. The method of preparation of the catalyst comprises the following steps: (1) combination and mixing of the catalyst constituents; (2) drying to obtain a mixture; (3) heating the mixture to 600 to 800° C. at a heating rate of 1 to 4° C. per minute and calcining at a temperature between 600 and 800° C. for 6 to 8 hours to obtain a product in powder form; and (4) milling the product powder and treatment by a pressure impregnation method to obtain the target product.

CN 102513124 A discloses a technology for the production of synthetic natural gas by methanation of carbon oxides and provides a catalyst for the methanation of coke oven gas and a method of preparation thereof. The catalyst is a γ-alumina or a titanium dioxide support to stabilize the active component and an additive, wherein the active component is Ni and the additive consists of a first additive and a second additive; the first additive is a rare earth element and the second additive one or a combination of two or more of Sr, Mn, V, Zr, Ce, and Cr.

CN 102463120 A discloses a catalyst containing nickel and manganese and its preparation and use. The catalyst containing nickel and manganese contains a) nickel oxide, wherein the nickel content is in the range from 15 to 55% by weight and b) manganese oxide, wherein the manganese content is in the range from 0.1 to 15% by weight. At least one of alumina, silica, titanium dioxide, and zirconium dioxide is used as catalyst support. The method of preparation comprises steps of dissolving a nickel salt and a manganese salt in an organic acid solution, wetting the catalyst support with the mixed solution obtained in the previous step, drying in a thermolysis to obtain the nickel- and manganese-containing catalyst. The organic acid solution is an organic carboxylic acid or a reducing organic acid, wherein the molar ratio of the overall charge of the carboxyl ions of the organic acid to the metal ions is between 0.5 to 3:1 and the molar ratio of the reducing organic acid to the metal ions is 0.2 to 2:1.

CN 102463119 A discloses a methanation catalyst and its preparation. The methanation catalyst comprises the following components: a) nickel oxide, wherein the nickel content is between 5 and 50% by weight; b) manganese oxide, wherein the manganese content is from 0.1 to 15% by weight; c) at least one of the oxides of beryllium, manganese, calcium, strontium, barium, lanthanum, and cerium, wherein the metal content is between 0.5 and 20% by weight, with component c) distributed throughout the support particles. The disclosed preparation comprises the following steps: 1) combined dissolution of a nickel salt and/or a manganese salt in an organic acid, preparation of a salt of component c) in an aqueous solution; and 2) wetting the components to be stabilized, the nickel, the manganese, and component c), wherein component c) is stabilized independently, and calcining and a sintering/disintegration treatment is carried out after each stabilization.

CN 103706366 A discloses a catalyst comprising 15 to 55% of an active component, 1 to 6% of a first catalytic promoter, 3 to 15% of a second catalytic promoter, the balance being a catalyst support, wherein the active component is nickel oxide, the catalytic support is $Al_2O_3$, the first catalytic promoter is one selected from lanthanum oxide, cerium oxide or samarium oxide, and the second catalytic promoter is at least one from magnesium oxide, manganese oxide, iron oxide, and zirconium oxide. The method of preparation comprises the steps: dissolution of a reductant in water to obtain a reducing solution, mixing nickel nitrate, aluminum nitrate, the first metal salt, and the second metal salt into water to obtain a raw material solution, and addition of the reducing mixture to the starting material solution with steady stirring to obtain a first solution, transfer to a sealed reactor and performance of a reaction at 100 to 200° C. for 10 to 15 hours, cooling to room temperature, filtering and washing to a pH of 6 to 7, drying at 80 to 120° C. for 4 to 30 hours, and calcining at 300 to 550° C. for 2 to 12 hours to obtain a catalyst, wherein the reductant is one selected from formaldehyde, hydrazine hydrate, sodium hypophosphite, and ascorbic acid, where the first metal salt is one selected from lanthanum nitrate, cerium nitrate, and samarium nitrate, the second metal salt is at least one selected from magnesium nitrate, manganese nitrate, iron nitrate, and zirconium nitrate, and the alkali solution is an aqueous solution of sodium carbonate, sodium hydroxide, potassium carbonate, ammonium carbonate, urea or $NH_3 \cdot H_2O$. The catalyst may be mixed with a binder (calcium aluminate), a lubricant (graphite), and water and then pressed into particle form. The catalyst is suitable for the methanation of coal gas at high temperature and high pressure in order to produce synthetic natural gas.

CN 104028270 A discloses a methanation catalyst comprising 5 to 60% by weight of a catalytically active NiO component, based on the total weight of catalyst, the balance comprising $Al_2O_3$, which can likewise contain 1 to 25% by weight, based on the total weight of catalyst, of a co-catalyst component M, wherein the co-catalyst component M is selected from one or more oxides of the metals Ce, Ca, Co, La, Sm, Zr, Ba, Mn, Fe, Mo, Ti and Cu. The document also provides a method for preparing the methanation catalyst; this comprises mixing of the precursor for the catalytically active component, of the precursor for the co-catalyst component M, and of a catalyst support according to the corresponding proportion in the methanation catalyst composition, addition of an organic fuel, thorough mixing and drying to form a gel-like product, performance of a combustion reaction, cleaning, and drying to obtain the final product.

CN 101745401 A discloses a supported, sulfur-resistant methanation catalyst which features a main metal M as active component, a second metal M1 as adjuvant, and S as support material, wherein the weight ratio between M1, M, and S is 0.01 to 39:1 to 30:0.01 to 90, M is Mo, W, and/or V, the second metal M1 is one or more of Fe, Co, Ni, Cr, Mn, La, Y, or/and Ce, and the support S is $ZrO_2$, $Al_2O_3$, MgO or $TiO_2$. The supported, sulfur-resistant methanation catalyst is prepared by a sol-gel method.

It is an object of the invention to provide a methanation catalyst for the methanation of carbon monoxide and/or carbon dioxide that, alongside high selectivity and stability, shows improved activity compared with catalysts of the prior art.

This object is achieved by a catalyst for the methanation of carbon monoxide and/or carbon dioxide comprising aluminum oxide, a Ni active mass, and Mn, wherein the Ni/Mn molar ratio in the catalyst is 3.0 to 10.0, preferably 4.0 to 9.0, and more preferably 5.5 to 6.5.

The Ni/Mn ratio can also be in the range from 6.0 to 10.0, preferably in the range from 7.0 to 9.0, and most preferably in the range from 7.5 to 8.5.

The aluminum oxide does not need to be stoichiometric $Al_2O_3$, but can instead also be non-stoichiometric aluminum oxide.

The promoter Mn may be present wholly or partly in the Ni active mass. The catalyst may contain further promoters besides Mn, but likewise may contain exclusively Mn as promoter. The oxidation states of Al, Ni, and the promoters may vary according to how the catalyst is treated. Al, Ni, and the promoters are typically present as metal cations (e.g. $Al^{3+}$, $Ni^{2+}$, $Mn^{2+}$, $Mn^{3+}$, $Mn^{4+}$). After calcination, for example in air, high oxidation states or the maximum oxidation states may be reached. If the catalyst is reduced at temperatures above room temperature, for example under reaction conditions with hydrogen, Al, Ni, and the promoters may adopt lower oxidation states or be partly or completely present in oxidation state 0. The charge of the metal cations is counterbalanced by oxygen anions ($O^{2-}$).

The catalyst according to the invention may contain further components besides aluminum oxide ($AlO_x$, where $x \leq 1.5$), Ni, and Mn (and the oxygen anions needed to counterbalance the charge), but it may also consist exclusively of aluminum oxide, Ni, and Mn. The Ni active mass may likewise contain further promoters besides Mn, including for example Fe, but it may also contain exclusively the promoter Mn. The Ni active mass preferably contains none of the elements Ta, In, Cu, Ce, Cr, Bi, Fe, P, Sb, Sn, B, Si, Ti, Zr, Co, Rh, Ru, Ag, Ir, Pd, and Pt. The Ni active mass preferably does not contain any noble metal.

The Al/Ni atomic ratio may be between 0.5 and 1.5, preferably between 0.8 and 1.2; the Al/Ni ratio is more preferably approximately 1.

The catalyst according to the invention may advantageously contain, in the Ni active mass, crystallites with a diameter below 20 mm, preferably below 10 mm. The Ni active mass may even consist entirely or in substantial parts of crystallites with a diameter below 20 mm, preferably below 10 mm. The Ni active mass is preferably in a metallic state.

The $CO_2$ uptake capacity of the catalysts at 35° C. may be greater than 150 µmol/g and is preferably in the range from 150 to 350 µmol/g, more preferably from 180 to 260 µmol/g.

The BET surface area ($S_{BET}$) of the catalyst according to the invention may be greater than 100 m²/g, preferably greater than 200 m²/g, or in the range from 200 to 400 m²/g, preferably in the range from 200 to 300 m²/g, and especially preferably in the range from 200 to 250 m²/g.

The specific metal surface area ($S_{met}$) of the catalyst according to the invention is preferably greater than 5 m²/g, preferably greater than 10 m²/g or in the range from 10 to 30 m²/g, preferably in the range from 15 to 25 m²/g or in the range from 17 to 23 m²/g.

The invention also relates to a method for the preparation of a methanation catalyst comprising the steps:
 a) co-precipitation from a solution containing Al, Ni, and Mn in dissolved form to obtain a precipitate,
 b) isolation of the precipitate from step a),
 c) drying of the isolated precipitate from step b), and
 d) calcining of the dried precipitate from step c).

The solution from step a) here is preferably an aqueous solution and Al, Ni, and Mn are present in the aqueous solution as dissolved ionic compounds.

Al is dissolved preferably as aluminum nitrate, aluminum trichloride or aluminum sulfate. Ni is dissolved preferably as nickel nitrate, nickel dichloride, nickel sulfate, nickel acetate or nickel carbonate. Mn is preferably present in oxidation state II or IV and dissolved as manganese nitrate, manganese acetate, manganese dichloride, manganese sulfate or else in oxidation state VII as permanganate ion.

Co-precipitation is carried out by addition of the solution containing Al, Ni, and Mn to an initial change of a basic solution or by addition of a basic solution to the initially charged solution containing Al, Ni, and Mn. Alternatively, the solution containing Al, Ni, and Mn and the basic solution are simultaneously added to a vessel already containing a solvent such as water and mixed therein. The basic solution has a pH greater than 7, preferably in the range from 8 to 10, and preferably contains an alkali metal hydroxide and/or an alkali metal carbonate, for example a mixture of sodium hydroxide and sodium carbonate. The co-precipitation is carried out preferably with temperature regulation so that the temperature of the solution is close to room temperature or, for example, 30° C.

Al, Ni, and Mn are preferably in dissolved form, present in the aqueous solution as ionic compounds, and have the same anion, which may for example be nitrate.

After the precipitation (co-precipitation), the precipitate is preferably aged in the solution for at least 30 minutes, preferably for longer than 1 hour, and more preferably for longer than 12 hours. The ageing is preferably carried out by stirring the precipitate in the solution (mother liquor) at approximately room temperature.

The precipitate obtained by co-precipitation is isolated, for example by conducting a filtration. The filtration may suitably be carried out using, for example, a filter press.

The isolated precipitate is preferably washed to neutral pH, for example with distilled water.

The isolated precipitate may subsequently be dried, for example at elevated temperature in air. Drying is preferably carried out at a temperature between 70° C. and 90° C. for a period longer than 4 hours, preferably longer than 12 hours.

The isolated precipitate is calcined; this can be carried out in air at a temperature between 300° C. and 600° C., preferably at 400° C. to 500° C., and for a period of 3 hours to 10 hours, preferably 5 to 7 hours.

The catalyst according to the invention is to be used especially in the methanation of carbon monoxide and/or carbon dioxide. The methanation of carbon dioxide can be represented by the following reaction equation:

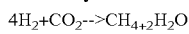

The methanation of carbon monoxide can be represented by the following reaction equation:

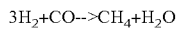

In the process for performing the methanation, the reaction gas which contains carbon dioxide and/or carbon monoxide or a mixture of the two is brought into contact with the catalyst at a temperature above 200° C.

FIGS. 1 to 4 show the catalytic profile of the manganese-doped catalysts Mn1, Mn4, Mn6, and Mn8 before and after ageing.

Figure 5:
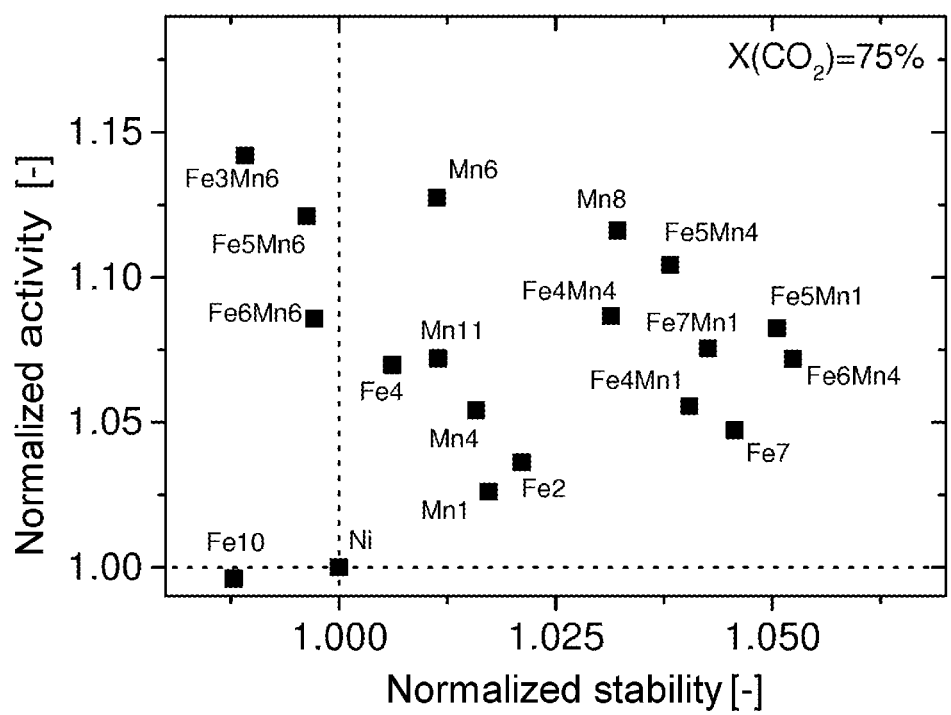

FIG. 1: Catalytie test results for Mn1 (comparative example)
FIG. 2: Catalytie test results for Mn4 (example)
FIG. 3: Catalytie test results for Mn6 (example)
FIG. 4: Catalytie test results for Mn8 (comparative example)
FIG. 5: Activity/stability diagram for the described samples.

METHODS

Elemental Analysis

The composition of the calcined catalysts was determined by inductively-coupled plasma optical emission spectroscopy (ICP-OES). 50 mg of catalyst was dissolved in 50 ml of 1 molar phosphoric acid (VWR, analytical grade) at 60° C. To dissolve the manganese dioxide that forms, 50 mg of $Na_2SO_3$ (Sigma-Aldrich, analytical grade) was added to the solution. The solutions were cooled and then diluted 1/10 and filtered through 0.1 µm filters (Pall). The calibration solutions were made up at concentrations of 1, 10, and 50 mg l$^{-1}$ (Merck). The metal concentrations were determined using an Agilent 700 ICP-OES.

Determination of Specific Surface Area

The specific surface areas of the catalysts ($S_{BET}$) were determined by $N_2$-BET analysis on a Nova 4000e (Quantachrome). For this, 100 mg of catalyst was degassed for 3 hours at 120° C. and adsorption and desorption isotherms were then recorded in the 0.007 to 1 p/p$_0$ range. The BET surface area was determined using the data points in the 0.007 to 0.28 p/p$_0$ range.

Chemisorption

Chemisorption experiments were carried out on an Autosorb 1C (Quantachrome). Before measurement, 100 mg of catalyst was activated at 500° C. in 10% $H_2$ in $N_2$ for 6 hours. The heating ramp was 2 K min$^{-1}$.

The metal surface area ($S_{MET}$) was determined in accordance with DIN 66136-2 (vers. 2007-01) by $H_2$ chemisorption at 35° C. For this purpose, 20 adsorption points were recorded equidistantly from 40 mmHg to 800 mmHg. The equilibration time was 2 min for adsorption and 10 min for thermal equilibration. For the determination of the metal surface area, the metal atom/H stoichiometry was set at 1. For the $CO_2$ chemisorption measurements to determine the $CO_2$ uptake capacity (U($CO_2$)), the equilibration time for adsorption was set at 10 min with the parameters otherwise unchanged. Before recording the chemisorption data, any kinetic inhibition of $CO_2$ chemisorption under these conditions was ruled out experimentally. Metal surface areas and $CO_2$ uptake capacities were extrapolated to a pressure of 0 mmHg by the extrapolation method.

Synthesis

The catalysts were prepared by co-precipitation, with the nickel/aluminum atomic ratio set at 1. To investigate the effect of iron on the behavior of the catalyst, iron(III) nitrate was added to the nickel nitrate/aluminum nitrate salt solution during the synthesis of the catalyst. To investigate the concomitant effect of iron and manganese on the behavior of the catalyst, manganese(II) nitrate and iron(III) nitrate were added to the nickel nitrate/aluminum nitrate salt solution during the synthesis of the catalyst. All chemicals used were of analytical grade purity. Water was purified in a Millipore filter system and the purity verified by conductivity measurements. The synthesis was carried out in a double-jacketed stirred-tank reactor with a capacity of 3 l. The thermostat fitted to the water-filled double jacket allowed the temperature to be maintained at 30° C. during the synthesis run and two baffles were employed for better mixing. Stirring was carried out using a precision glass stirrer operating at 150 rpm. For the synthesis, the stirred-tank reactor was charged with 1 l of $H_2O$, which was adjusted to pH 9±0.1. The addition of the mixture of dissolved nitrates was carried out at a rate of 2.5 ml min$^{-1}$. The controlled addition of the precipitation reagent at the same time served to maintain the pH. The starting materials used were one-molar solutions of the respective nitrates ($Ni(NO_3)_2 \cdot 6H_2O$, $Al(NO_3)_2 \cdot 9H_2O$, $Fe(NO_3)_3 \cdot 9H_2O$, and $Mn(NO_3)_2 \cdot 4H_2O$). These were mixed, as shown in Table 2, to a total volume of 120 ml min$^{-1}$ before undergoing dropwise addition to the reactor. The precipitation reagent used was a mixture of equal volumes of 0.5 M NaOH and 0.5 M $Na_2CO_3$ solutions, which was added using a titrator. The suspension was aged overnight in the mother liquor with constant stirring, after which the precipitate was filtered off and washed with $H_2O$ until the filtrate was of neutral pH. After drying overnight at 80° C. in a drying cabinet, the dried precipitate (precursor) was heated to 450° C. at a heating rate of 5 K min$^{-1}$ and calcined for 6 hours in synthetic air.

Activity and Stability Measurement

In order to be able to compare different catalysts in terms of their $CO_2$ methanation activity, a test program was developed that information on their activity and stability. For this, 25 mg of catalyst from the 150-200 μm sieve fraction was diluted with nine times the amount of SiC and placed in the reactor. The successive measurement steps performed—reduction, equilibration, S-curve 1, ageing, S-curve 2—are shown in detail in Table 1.

TABLE 1

Parameters for the measurement steps for determination of the activity and stability profile

| | Reaction gas, ratio $H_2/CO_2/Ar$ | Reaction gas Q [l (STP) $g_{cat}^{-1}$ h$^{-1}$] | T [° C.] | $p_{abs}$ [bar] | Duration [h] |
|---|---|---|---|---|---|
| Reduction | 5/0/95 | 130 | 485 | 1 | 8 |
| Equilibration | 4/1/5 | 150 | 260 | 7 | 24 |
| S-curve 1 | 4/1/5 | 150 | 170-500 | 8 | — |
| Ageing | 4/1/5 | 150 | 500 | 7 | 32 |
| S-curve 2 | 4/1/5 | 150 | 170-500 | 8 | — |

To determine the temperature-$CO_2$ conversion curves, the temperature was increased in 25° C. increments in the specified range and the activity in each case determined. A comparison of the two S-curves before and after ageing for 32 hours at 500° C. gives an insight into the stability of the systems to high temperatures.

As a measure of the activity, on a representative basis, the temperature T75.1 necessary to achieve a $CO_2$ conversion of 75% during the S-curve 1 measurement step was determined. For this, the temperature was increased in 25° C. increments in the specified range. The lower T75.1 is, the higher therefore the activity of the catalyst.

As a measure of the activity after ageing, on a representative basis, the temperature T75.2 necessary to achieve a $CO_2$ conversion of 75% during the S-curve 2 measurement step was determined. For this, the temperature was increased in 25° C. increments in the specified range. The lower T75.2 is, the higher therefore the activity of the catalyst after ageing.

Calculation of the difference between T75.1 and T75.2 from the two conversion temperature characteristics gives a measure of the stability of the catalyst. Here too, the smaller the difference, the more stable the catalyst. For better comparability, all calculated activities and stabilities were normalized with reference to the nickel-aluminum oxide catalyst without promoter (Ni). The normalized activity and stability are given by the following expressions:

$$\text{Normalized activity} = \frac{T_{75.1}(Ni/AlO_x)}{T_{75.1}(dop.cat.)}$$

$$\text{Normalized stability} = \frac{\frac{T_{75.2}(Ni/AlO_x)}{T_{75.1}(Ni/AlO_x)}}{\frac{T_{75.2}(dop.cat.)}{T_{75.1}(dop.cat.)}}$$

The results in FIGS. 1 to 4 show that addition of a manganese promoter to a Ni/$AlO_x$ catalyst results in a significant increase in catalyst activity.

EXAMPLES

TABLE 2

Molar metal salt solutions used in the co-precipitation

| Example No. | Catalyst | $V_{Ni(NO3)2}$ [ml] | $V_{Al(NO3)2}$ [ml] | $V_{Fe(NO3)3}$ [ml] | $V_{Mn(NO3)2}$ [ml] |
|---|---|---|---|---|---|
| Comparative examples | | | | | |
| 1 | Ni | 60.0 | 60.0 | | |
| 2 | Fe2 | 59.0 | 59.0 | 2.0 | |
| 3 | Fe4 | 57.0 | 57.0 | 6.0 | |
| 4 | Fe7 | 55.0 | 55.0 | 10.0 | |
| 5 | Fe10 | 52.5 | 52.5 | 15.0 | |
| 6 | Mn1 | 59 | 59 | — | 2 |
| 7 | Mn4 | 57 | 57 | — | 6 |
| 8 | Mn11 | 51 | 51 | — | 18 |
| 9 | Fe4Mn4 | 54.29 | 54.29 | 5.71 | 5.71 |
| 10 | Fe4Mn1 | 56.10 | 56.10 | 5.90 | 1.90 |
| 11 | Fe5Mn4 | 53.38 | 53.38 | 7.63 | 5.62 |
| 12 | Fe5Mn1 | 55.13 | 55.13 | 7.88 | 1.87 |
| 13 | Fe6Mn4 | 52.47 | 52.47 | 9.54 | 5.52 |
| 14 | Fe7Mn1 | 54.16 | 54.16 | 9.85 | 1.84 |
| Examples | | | | | |
| 1 | Mn6 | 55 | 55 | — | 10 |
| 2 | Mn8 | 52.5 | 52.5 | — | 15 |
| 3 | Fe3Mn6 | 52.47 | 52.47 | 5.52 | 9.54 |
| 4 | Fe5Mn6 | 51.62 | 51.62 | 7.37 | 9.39 |
| 5 | Fe6Mn6 | 50.77 | 50.77 | 9.23 | 9.23 |

TABLE 3

Composition of the calcined catalysts

| | | Element contents [%] [% by wt.] | | | | Atomic ratios | | |
|---|---|---|---|---|---|---|---|---|
| Example | Catalyst | Ni | Mn | Fe | Al | Ni/Al | Ni/Mn | Ni/Fe |
| Comparative examples | | | | | | | | |
| 1 | Ni | 44.3 | — | — | 19.8 | 1.03 | — | — |
| 2 | Fe2 | 40.0 | — | 1.7 | 19.4 | 0.95 | — | 22.0 |
| 3 | Fe4 | 39.7 | — | 4.3 | 19.4 | 0.94 | — | 8.8 |
| 4 | Fe7 | 39.6 | — | 6.9 | 17.3 | 1.05 | — | 5.4 |
| 5 | Fe10 | 36.1 | — | 10.1 | 17.9 | 0.93 | — | 3.4 |
| 6 | Mn1 | 38.7 | 1.3 | — | 18.0 | 0.99 | 27.3 | — |
| 7 | Mn4 | 38.9 | 3.7 | — | 18.2 | 0.98 | 9.8 | — |
| 8 | Mn11 | 34.0 | 10.8 | | 16.2 | 0.97 | 3.0 | — |
| 9 | Fe4Mn4 | 39.9 | 17.8 | 4.2 | 4.0 | 1.03 | 9.0 | 9.5 |
| 10 | Fe4Mn1 | 39.5 | 17.7 | 1.3 | 3.9 | 1.03 | 28.9 | 9.7 |
| 11 | Fe5Mn4 | 38.1 | 17.3 | 3.8 | 5.3 | 1.01 | 9.4 | 6.8 |
| 12 | Fe5Mn1 | 38.7 | 17.4 | 1.2 | 5.3 | 1.02 | 29.4 | 6.9 |
| 13 | Fe6Mn4 | 36.9 | 18.2 | 3.5 | 6.2 | 0.93 | 9.8 | 5.6 |
| 14 | Fe7Mn1 | 37.2 | 16.0 | 1.3 | 6.5 | 1.07 | 26.5 | 5.4 |
| Examples | | | | | | | | |
| 1 | Mn6 | 36.3 | 6.1 | — | 15.5 | 1.08 | 5.6 | — |
| 2 | Mn8 | 31.9 | 8.3 | — | 15.2 | 0.97 | 3.6 | — |
| 3 | Fe3Mn6 | 35.6 | 16.0 | 6.0 | 3.4 | 1.02 | 6.0 | 10.0 |
| 4 | Fe5Mn6 | 36.3 | 16.6 | 6.1 | 4.8 | 1.01 | 5.5 | 7.2 |
| 5 | Fe6Mn6 | 34.1 | 16.8 | 5.8 | 5.9 | 0.93 | 5.5 | 5.5 |

TABLE 4

Characterization data for the catalysts

| Example | Catalyst | $S_{BET}^a$ [m² $g_{cat}^{-1}$] | $S_{met}^a$ [m² $g_{cat}^{-1}$] | $U(CO_2)^a$ [μmol $g_{cat}^{-1}$] |
|---|---|---|---|---|
| Comparative examples | | | | |
| 1 | Ni | 209 | 21.1 | 172 |
| 2 | Fe2 | 227 | 19.8 | 199 |
| 3 | Fe4 | 244 | 18.3 | 198 |
| 4 | Fe7 | 216 | 11.4 | 196 |
| 5 | Fe10 | 250 | 9.3 | 188 |
| 6 | Mn1 | 211 | 19.2 | 197 |
| 7 | Mn4 | 223 | 20.1 | 215 |
| 8 | Mn11 | 213 | 10.8 | 242 |
| 9 | Fe4Mn4 | 275 | 12.9 | 345 |
| 10 | Fe4Mn1 | 241 | 16.1 | 204 |
| 11 | Fe5Mn4 | 238 | 17.8 | 298 |
| 12 | Fe5Mn1 | 251 | 17.6 | 269 |
| 13 | Fe6Mn4 | 262 | 7.6 | 276 |
| 14 | Fe7Mn1 | 237 | 11.2 | 223 |
| Examples | | | | |
| 1 | Mn6 | 231 | 20.0 | 244 |
| 2 | Mn8 | 214 | 17.6 | 240 |
| 3 | Fe3Mn6 | 249 | 11.9 | 277 |
| 4 | Fe5Mn6 | 268 | 15.8 | 327 |
| 5 | Fe6Mn6 | 239 | 5.5 | 322 |

*normalized to mass of the calcined catalyst

TABLE 5

Results for the catalytic test reaction

| Example | Catalyst | $T_{75.1}$ [° C.] | $T_{75.2}$ [° C.] | $T_{75.2}/T_{75.1}$ | Normalized activity | Normalized stability |
|---|---|---|---|---|---|---|
| Comparative examples | | | | | | |
| 1 | Ni | 289.41 | 314.11 | 1.085 | 1.000 | 1.000 |
| 2 | Fe2 | 279.29 | 296.86 | 1.063 | 1.036 | 1.021 |
| 3 | Fe4 | 275.05 | 293.37 | 1.067 | 1.052 | 1.018 |
| 4 | Fe7 | 276.35 | 286.84 | 1.038 | 1.047 | 1.046 |
| 5 | Fe10 | 290.54 | 319.21 | 1.099 | 0.996 | 0.998 |
| 6 | Mn1 | 282.04 | 300.91 | 1.067 | 1.026 | 1.017 |
| 7 | Mn4 | 274.57 | 293.36 | 1.068 | 1.054 | 1.016 |
| 8 | Mn11 | 269.95 | 289.67 | 1.073 | 1.072 | 1.011 |
| 9 | Fe4Mn4 | 266.34 | 280.27 | 1.052 | 1.087 | 1.031 |
| 10 | Fe4Mn1 | 274.18 | 286.01 | 1.043 | 1.056 | 1.040 |
| 11 | Fe5Mn4 | 264.02 | 275.09 | 1.042 | 1.096 | 1.042 |
| 12 | Fe5Mn1 | 262.62 | 271.83 | 1.035 | 1.102 | 1.049 |
| 13 | Fe6Mn4 | 270.01 | 278.48 | 1.031 | 1.072 | 1.052 |
| 14 | Fe7Mn1 | 269.11 | 280.15 | 1.041 | 1.075 | 1.043 |

TABLE 5-continued

Results for the catalytic test reaction

| Example | Catalyst | $T_{75.1}$ [° C.] | $T_{75.2}$ [° C.] | $T_{75.2}/T_{75.1}$ | Normalized activity | Normalized stability |
|---|---|---|---|---|---|---|
| | | | Examples | | | |
| 1 | Mn6 | 256.71 | 275.50 | 1.073 | 1.127 | 1.011 |
| 2 | Mn8 | 259.31 | 272.67 | 1.052 | 1.116 | 1.032 |
| 3 | Fe3Mn6 | 253.42 | 278.06 | 1.097 | 1.142 | 0.989 |
| 4 | Fe5Mn6 | 258.16 | 281.24 | 1.089 | 1.121 | 0.996 |
| 5 | Fe6Mn6 | 266.56 | 290.13 | 1.088 | 1.086 | 0.997 |

The invention claimed is:

1. A catalyst for the methanation of carbon monoxide and/or carbon dioxide, comprising aluminum oxide, a Ni active mass, and Mn, and having a Ni/Mn molar ratio in the range of 4.0-6.5 and a Al/Ni molar ratio in the range of 0.5 to 1.5.

2. The catalyst as claimed in claim 1, wherein the Ni active mass contains crystallites with a diameter below 20 mm.

3. The catalyst as claimed in claim 1, having a $CO_2$ uptake capacity at 35° C. of greater than 200 μmol/g.

4. The catalyst of claim 1, wherein the Ni/Mn molar ratio is 5.5 to 6.5.

5. The catalyst as claimed in claim 1, having an Al/Ni atomic ratio between 0.8 and 1.2.

6. The catalyst as claimed in claim 1, wherein the Ni active mass contains none of the elements Ta, In, Cu, Ce, Cr, Bi, Fe, P, Sb, Sn, B, Si, Ti, Zr, Co, Rh, Ru, Ag, Ir, Pd, and Pt.

7. The catalyst as claimed in claim 1, wherein the Ni active mass contains Fe and Mn.

8. The catalyst as claimed in claim 7, wherein the Ni active mass contains none of the elements Ta, In, Cu, Ce, Cr, Bi, P, Sb, Sn, B, Si, Ti, Zr, Co, Rh, Ru, Ag, Ir, Pd, and Pt.

9. The catalyst as claimed in claim 1, wherein metals of the Ni active mass consist essentially of Ni and Mn.

10. The catalyst as claimed in claim 1, wherein metals of the Ni active mass consist essentially of Ni, Mn and Fe.

11. A catalyst for the methanation of carbon monoxide and/or carbon dioxide, comprising aluminum oxide, a Ni active mass, Mn and Fe, and having a Ni/Mn molar ratio in the range of 3.0-10.0 and a Al/Ni molar ratio in the range of 0.5 to 1.5.

12. A catalyst according to claim 11, having an Ni/Fe ratio in the range of 5.5-10.0.

* * * * *